(12) United States Patent
Rust et al.

(10) Patent No.: US 7,615,072 B2
(45) Date of Patent: Nov. 10, 2009

(54) ENDOLUMINAL PROSTHESIS

(75) Inventors: Matthew Rust, Santa Rosa, CA (US); Trevor Greenan, Santa Rosa, CA (US); Frank Yang, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 403 days.

(21) Appl. No.: 11/559,723

(22) Filed: Nov. 14, 2006

(65) Prior Publication Data

US 2008/0114441 A1 May 15, 2008

(51) Int. Cl.
*A61F 2/06* (2006.01)
(52) U.S. Cl. ..................................................... 623/1.36
(58) Field of Classification Search ........ 623/1.11–1.35
See application file for complete search history.

(56) References Cited

U.S. PATENT DOCUMENTS

| | | | |
|---|---|---|---|
| 5,713,917 A | 2/1998 | Leonhardt et al. | |
| 5,824,041 A | 10/1998 | Lenker et al. | |
| 6,423,090 B1 * | 7/2002 | Hancock | 623/1.15 |
| 6,929,661 B2 * | 8/2005 | Bolduc et al. | 623/1.35 |
| 6,945,992 B2 * | 9/2005 | Goodson et al. | 623/1.13 |
| 7,331,992 B2 * | 2/2008 | Randall et al. | 623/1.36 |
| 2005/0222669 A1 * | 10/2005 | Purdy | 623/1.13 |
| 2007/0055345 A1 * | 3/2007 | Arbefeuille | 623/1.13 |
| 2007/0142894 A1 * | 6/2007 | Moore et al. | 623/1.12 |

* cited by examiner

*Primary Examiner*—Suzette J Gherbi
(74) *Attorney, Agent, or Firm*—Leslie Wilson

(57) ABSTRACT

An endoluminal prosthesis including a tubular graft having a proximal end and a distal end; a suprarenal spring stent operably connected to the proximal end, the suprarenal spring stent having suprarenal positive apices and suprarenal negative apices connected in a sinusoidal ring pattern by suprarenal struts; and a sealing spring stent operably connected to the tubular graft, the sealing spring stent having sealing positive apices, sealing negative apices, and intermediate sealing negative apices connected in a ring pattern, the sealing negative apices alternating with the intermediate sealing negative apices between adjacent sealing positive apices, the sealing positive apices being connected to the sealing negative apices by sealing struts, and the sealing positive apices being connected to the intermediate sealing negative apices by intermediate sealing struts. The suprarenal positive apices are axially aligned with the intermediate sealing negative apices.

37 Claims, 7 Drawing Sheets

ENDOLUMINAL PROSTHESIS

TECHNICAL FIELD

The technical field of this disclosure is medical implantation devices, particularly, an endoluminal prosthesis.

BACKGROUND OF THE INVENTION

Wide ranges of medical treatments have been developed using endoluminal prostheses, which are medical devices adapted for temporary or permanent implantation within a body lumen, such as naturally occurring or artificially made lumens. Examples of lumens in which endoluminal prostheses may be implanted include arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed with particular structures to modify the mechanics of the targeted luminal wall.

A number of vascular devices have been developed for replacing, supplementing, or excluding portions of blood vessels. These vascular devices include endoluminal vascular prostheses and stent grafts. Aneurysm exclusion devices, such as abdominal aortic aneurysm (AAA) devices, are used to exclude vascular aneurysms and provide a prosthetic lumen for the flow of blood. Vascular aneurysms are the result of abnormal dilation of a blood vessel, usually from disease or a genetic predisposition, which can weaken the arterial wall and allow it to expand. Aneurysms can occur in any blood vessel, but most occur in the aorta and peripheral arteries, with the majority of aneurysms occurring in the abdominal aorta. An abdominal aortic aneurysm typically begins below the renal arteries and extends into one or both of the iliac arteries.

Aneurysms, especially abdominal aortic aneurysms, are commonly treated in open surgery procedures in which the diseased vessel segment is bypassed and repaired with an artificial vascular graft. While open surgery is an effective surgical technique in light of the risk of a fatal abdominal aortic aneurysm rupture, the open surgical technique suffers from a number of disadvantages. The surgical procedure is complex, requires a long hospital stay, requires a long recovery time, and has a high mortality rate. Less invasive devices and techniques have been developed to avoid these disadvantages. Tubular endoluminal prostheses that provide a lumen or lumens for blood flow while excluding blood flow to the aneurysm site are introduced into the blood vessel using a catheter in a less or minimally invasive technique. The tubular endoluminal prosthesis is introduced in a small diameter crimped condition and expanded at the aneurysm. Although often referred to as stent grafts, these tubular endoluminal prostheses differ from covered stents in that they are not used to mechanically prop open natural blood vessels. Rather, they are used to secure an artificial lumen in a sealing engagement with the vessel wall without further opening the abnormally dilated natural blood vessel.

Stent grafts typically include a support structure supporting a graft material, such as woven polymer materials, e.g., Dacron, or polytetrafluoroethylene (PTFE). The graft material is secured to the inner or outer diameter of the support structure, which supports the graft material and/or holds it in place against a luminal wall. The stent graft is secured to a vessel wall above and below the aneurysm. A suprarenal spring stent of the stent graft can be located above the aneurysm to provide a radial force which engages the lumen wall and seals the stent graft at the lumen wall. The suprarenal spring stent extends beyond the graft material, so that blood can flow to renal arteries located at the suprarenal spring stent. The suprarenal spring stent can include hooks to puncture the vessel wall and further secure the stent graft in place.

One shortcoming in present stent graft designs is the adequacy of sealing at the proximal end. Flow channels can form between the graft material and the lumen wall where the suprarenal spring stent is not holding the graft material in contact with the lumen wall. Blood flow enters the flow channel, rather than the stent graft lumen, thus continuing to stress the wall of the aneurysmal sac.

Another shortcoming in present stent graft designs is the inability to accommodate individual abdominal aortic aneurysm geometries, such as a short AAA neck, tortuosity in the AAA, or an angulated AAA. A short AAA neck can preclude use of a stent graft, because there is not room to seal the stent graft at the lumen wall. Tortuosity or angulation can prevent an adequate seal, make placement of an inflexible stents graft more difficult, and increase stress on the stent graft.

Yet another shortcoming in present stent graft designs is ease of deployment. The body spring stents are placed close together to keep the graft material between the body spring stents out of the stent graft lumen when the stent graft is deployed, but placing the body spring stents close together reduces the stent graft flexibility and make the stent graft more difficult to maneuver through the tortuous path to the AAA. In addition, the body spring stents are usually rings with a regular sinusoidal pattern, so that the apices of the rings line up when the body spring stents are crimped. This increases the bulk of the material at the level of the apexes and thereby the diameter of the crimped stent graft and makes it harder to maneuver into place.

Yet another shortcoming in present stent graft designs is ease of manufacture. Bifurcated stent grafts include an ipsilateral limb and a contralateral limb for deployment in the iliac arteries. The diameter of the ipsilateral limb is typically larger than the contralateral limb, so different limb spring stents are used, complicating manufacture. The contralateral limb spring stent must cleanly open the contralateral limb during deployment so that a guide wire can be advanced through the contralateral limb.

It would be desirable to have an endoluminal prosthesis that would overcome the above disadvantages.

SUMMARY OF THE INVENTION

One aspect according to the present invention provides an endoluminal prosthesis including a tubular graft having a proximal end and a distal end; a suprarenal spring stent operably connected to the proximal end, the suprarenal spring stent having suprarenal positive apices and suprarenal negative apices connected in a sinusoidal ring pattern by suprarenal struts; and a sealing spring stent operably connected to the tubular graft, the sealing spring stent having sealing positive apices, sealing negative apices, and intermediate sealing negative apices connected in a ring pattern, the sealing negative apices alternating with the intermediate sealing negative apices between adjacent sealing positive apices, the sealing positive apices being connected to the sealing negative apices by sealing struts, and the sealing positive apices being connected to the intermediate sealing negative apices by intermediate sealing struts. The suprarenal positive apices are axially aligned with the intermediate sealing negative apices.

Another aspect according to the present invention provides an endoluminal prosthesis including a tubular graft having a proximal end and a distal end; a suprarenal spring stent operably connected to the proximal end, the suprarenal spring stent having suprarenal positive apices and suprarenal negative apices connected in a sinusoidal ring pattern by suprarenal struts; and body spring stents operably connected to the tubular graft, each of the body spring stents having body positive apices, body intermediate negative apices, body intermediate positive apices, and body negative apices, connected in a ring pattern. Body struts connect the body negative apices to the body positive apices, first intermediate body struts connect the body positive apices to the body intermediate negative apices, second intermediate body struts connect the body intermediate negative apices to the body intermediate positive apices, and third intermediate body struts connect the body intermediate positive apices to the body negative apices.

Another aspect according to the present invention provides an endoluminal prosthesis including a tubular graft having a proximal end and a distal end, the tubular graft having a first iliac leg and a second iliac leg at the distal end, and an iliac bifurcation between the first iliac leg and the second iliac leg; a suprarenal spring stent operably connected to the proximal end, the suprarenal spring stent having suprarenal positive apices and suprarenal negative apices connected in a sinusoidal ring pattern by suprarenal struts; and body spring stents operably connected to the tubular graft, each of the body spring stents having body positive apices and body negative apices connected in a ring pattern with body struts. One of the body positive apices is axially aligned with the iliac bifurcation.

Another aspect according to the present invention provides an endoluminal prosthesis including a tubular graft having a proximal end; a suprarenal spring stent operably connected to the proximal end; and a sealing M spring stent operably connected to the tubular graft, the sealing M spring stent having M segments connected in a ring. The sealing M spring stent nests with the suprarenal spring stent.

Another aspect according to the present invention provides an endoluminal prosthesis including a tubular graft having a proximal end; a suprarenal spring stent operably connected to the proximal end; and modified M body spring stents operably connected to the tubular graft, each of the modified M body spring stents having modified M segments connected in a ring.

The foregoing and other features and advantages will become further apparent from the following detailed description of embodiments according to the invention, read in conjunction with the accompanying drawings. The detailed description and drawings are merely illustrative, rather than limiting.

DETAILED DESCRIPTION

Figure 1:
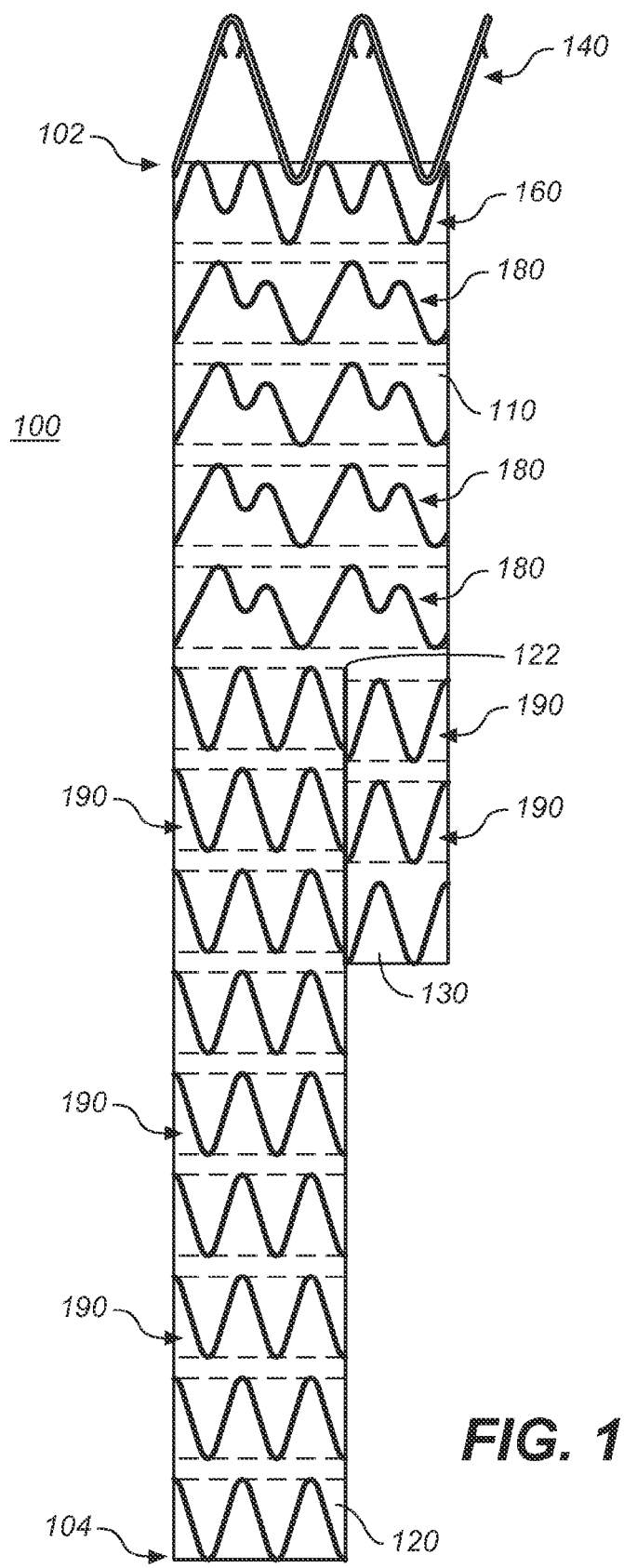
FIG. 1 is a side view of an endoluminal prosthesis made in accordance with the present invention.

FIG. 1 is a side view of an endoluminal prosthesis made in accordance with the present invention. The endoluminal prosthesis 100 includes a bifurcated tubular graft 110, a suprarenal spring stent 140, a sealing spring stent 160, and body spring stents 180 (dashed lines representing an imaginary line denoting the upper and lower limit of the distance between adjacent stents). The endoluminal prosthesis 100 has a proximal end 102 and a distal end 104. Proximal and distal designations are defined relative to the fluid flow in the lumen in which the stent graft is installed, with the flow being from proximal to distal. The suprarenal spring stent 140 is operably connected to the tubular graft 110 at the proximal end 102 of the tubular graft 110 to hold the tubular graft 110 open when the endoluminal prosthesis 100 is deployed. The suprarenal spring stent 140 is not covered by the tubular graft 110 so that blood can flow through the suprarenal spring stent 140 to the renal arteries when the suprarenal spring stent 140 is mounted across the renal arteries. The sealing spring stent 160 is operably connected to the tubular graft 110 near the proximal end 102 of the tubular graft 110 to seal the tubular graft 110 against the luminal wall of the vessel in which the endoluminal prosthesis 100 is deployed. The body spring stents 180 are operably connected to the tubular graft 110 along the length of the tubular graft 110 to hold open the lumen of the tubular graft 110 when the endoluminal prosthesis 100 is deployed. Those skilled in the art will appreciate that the suprarenal spring stent 140, sealing spring stent 160, and body spring stents 180 can be operably connected to the tubular graft 110 inside or outside of the lumen of the tubular graft 110.

In the example of FIG. 1, the endoluminal prosthesis 100 is a bifurcated stent graft including iliac legs 120, 130 and iliac spring stents 190 operably connected about the iliac legs 120, 130. An iliac bifurcation 122 is located between the first iliac leg 120 and the second iliac leg 130 where the first iliac leg 120 and the second iliac leg 130 separate. When the endoluminal prosthesis 100 is deployed, the iliac legs 120, 130 are located in (and/or direct blood flow into) the iliac arteries and the iliac spring stents 190 hold open the lumens of the iliac legs 120, 130.

Those skilled in the art will appreciate that the sealing spring stent 160 of FIG. 1 can be used with different types of body spring stents than the body spring stent 180 illustrated. Further, the body spring stents 180 of FIG. 1 can be used with different types of sealing spring stents than the sealing spring stent 160 illustrated. The sealing spring stent 160 and/or body spring stents 180 of FIG. 1 can be used with endoluminal prostheses other than a bifurcated stent graft.

Figure 2:
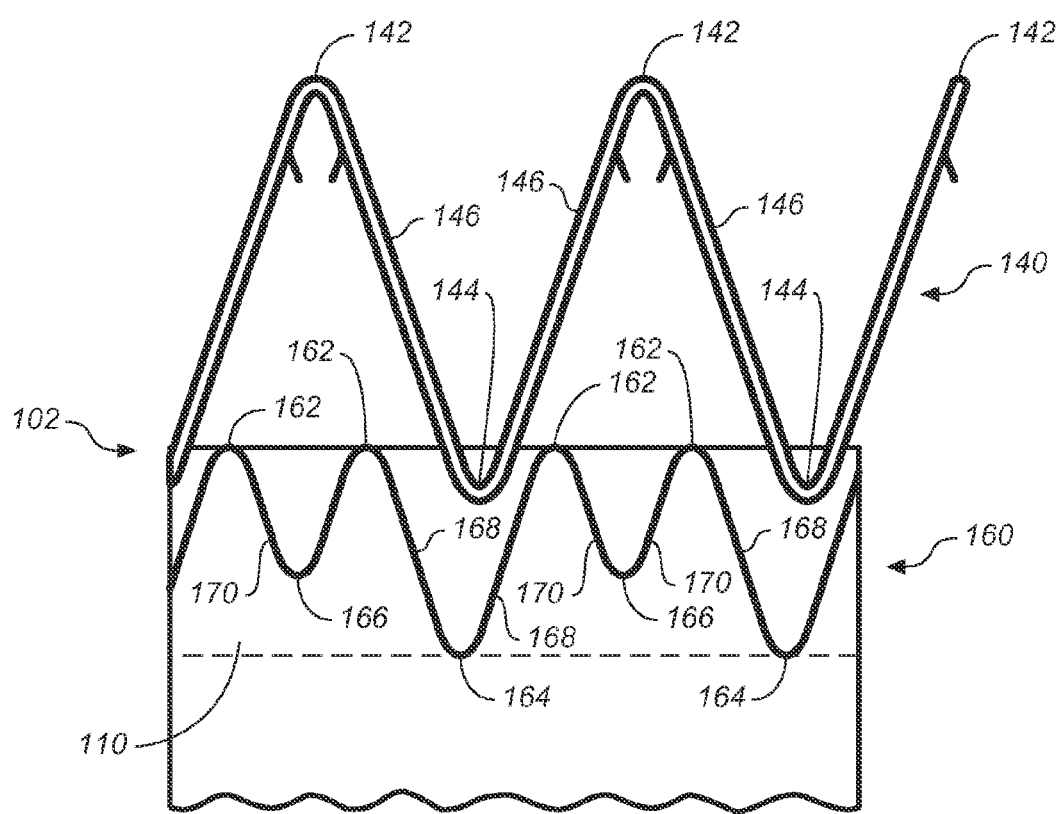
FIG. 2 is a detailed view of an endoluminal prosthesis with a sealing spring stent made in accordance with the present invention.
Figure 3:
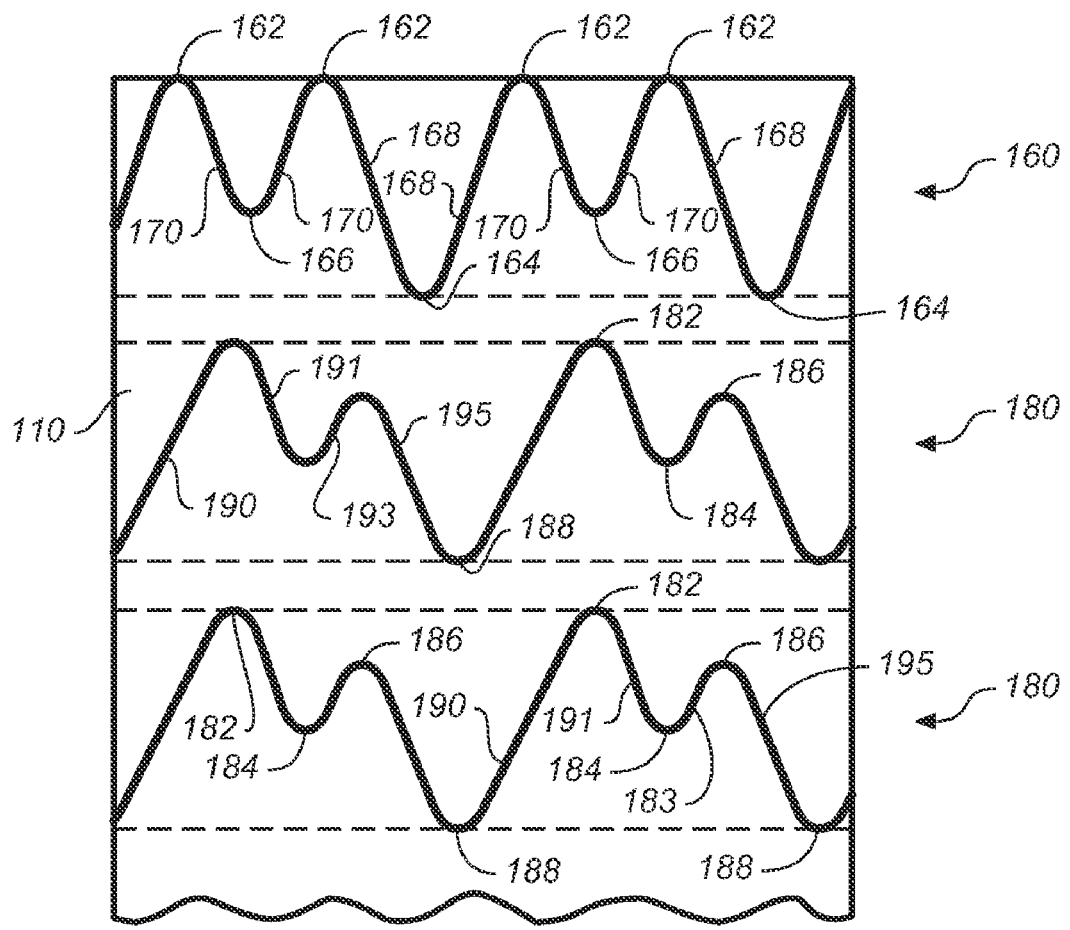
FIG. 3 is a detailed view of an endoluminal prosthesis with body spring stents made in accordance with the present invention.
Figure 4:
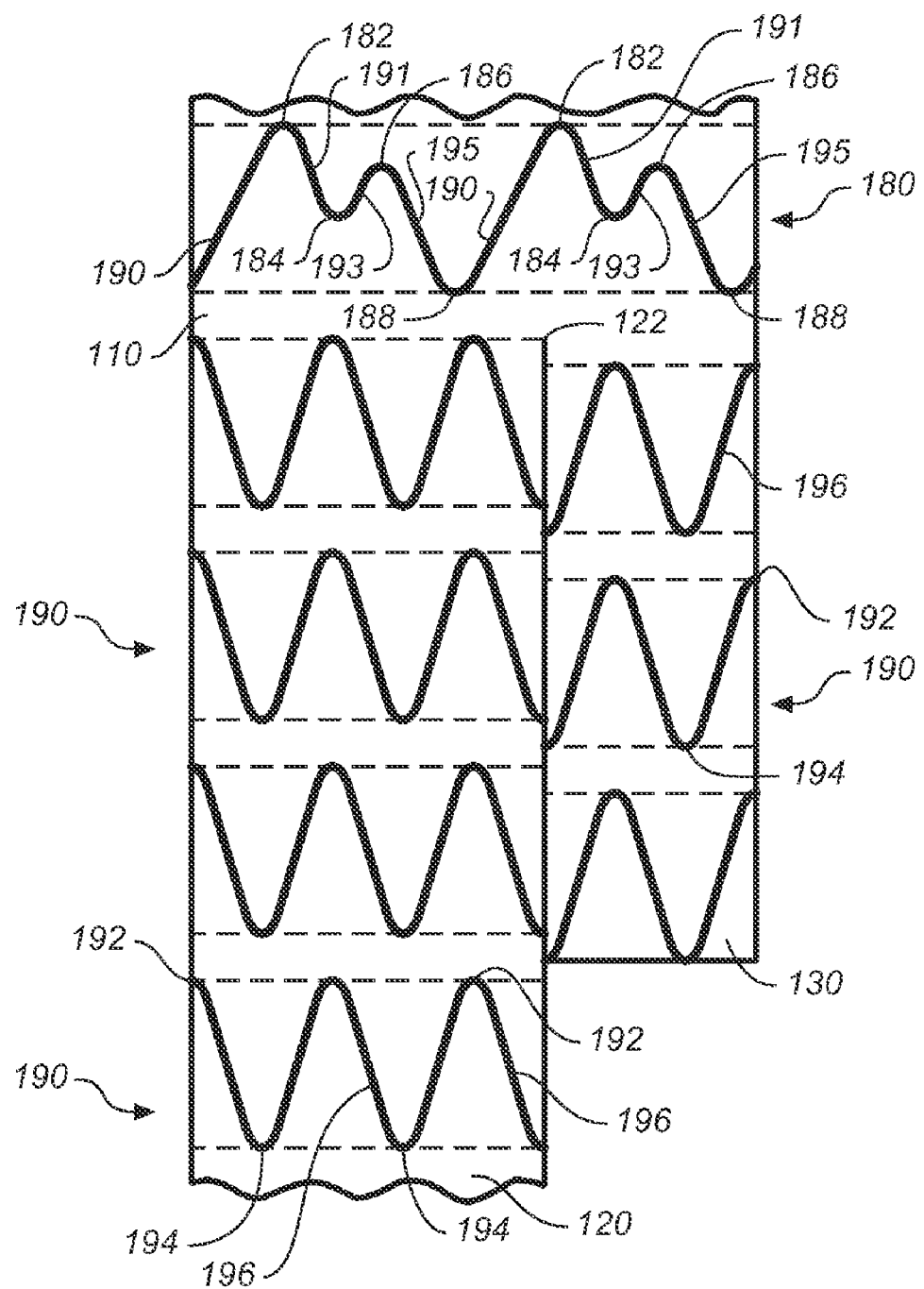
FIG. 4 is a detailed view of a bifurcated endoluminal prosthesis with iliac leg branches made in accordance with the present invention.

The spring stents are shaped and aligned to seal the tubular graft 110 against the luminal wall of the vessel while permitting the endoluminal prosthesis 100 to be compressed to a small diameter for delivery. FIGS. 2-4, in which like elements share like reference numbers with FIG. 1 and with each other, are detailed views of an endoluminal prosthesis illustrating the spring stents.

FIG. 2 is a detailed view of an endoluminal prosthesis with a sealing spring stent made in accordance with the present invention. The suprarenal spring stent 140 and the sealing spring stent 160 are arranged to seal the tubular graft 110 with a short landing area, i.e., a short axial length sealing the tubular graft 110 against the luminal wall of the vessel. The sealing spring stent 160 can be called a sealing M spring stent due to the M shape of the M segments between sealing negative apices 164. As defined herein, an M segment includes at least one intermediate negative apex between positive apices, which are connected to negative apices. The M segment can also include one or more intermediate positive apices.

The suprarenal spring stent 140 is operably connected to the tubular graft 110 at the proximal end 102 of the tubular graft 110 to hold the tubular graft 110 open when the endoluminal prosthesis 100 is deployed. The suprarenal spring stent 140 has suprarenal positive apices 142 and suprarenal negative apices 144 connected in a sinusoidal ring pattern by suprarenal struts 146.

The sealing spring stent 160 is operably connected to the tubular graft 110 near the proximal end 102 of the tubular graft 110 to seal the tubular graft 110 against the luminal wall of the vessel in which the endoluminal prosthesis 100 is deployed. The sealing spring stent 160 has sealing positive apices 162, sealing negative apices 164, and intermediate sealing negative apices 166. The sealing negative apices 164 alternate with the intermediate sealing negative apices 166 between adjacent sealing positive apices 162, i.e., the series of apices is positive—negative—positive—intermediate negative—positive . . . in a ring pattern. The sealing positive apices 162 are connected to the sealing negative apices 164 by sealing struts 168 and connected to the intermediate sealing negative apices 166 by intermediate sealing struts 170.

The suprarenal positive apices 142 are axially aligned with the intermediate sealing negative apices 166. The axial position of the intermediate sealing negative apices 166 near the proximal end 102 improves sealing at the proximal end 102 and reduces formation of flow channels between the tubular graft 110 and the lumen wall of the vessel. In one embodiment, the suprarenal negative apices 164 are circumferentially offset from the sealing positive apices 162. The circumferential offset decreases the diameter of the endoluminal prosthesis 100 when compressed since compression is limited by the number of positive and negative apices aligned along a given circumference. In another embodiment, the suprarenal negative apices 144 are axially aligned with the sealing negative apices 164.

FIG. 3 is a detailed view of an endoluminal prosthesis with body spring stents made in accordance with the present invention. The sealing spring stent 160 and the body spring stents 180 are arranged to help seal the tubular graft 110 against the luminal wall of the vessel. The sealing spring stent 160 is operably connected to the tubular graft 110 near the proximal end 102 of the tubular graft 110 to seal the tubular graft 110 against the luminal wall of the vessel in which the endoluminal prosthesis 100 is deployed. The body spring stents 180 can be called modified M spring stents due to the slanting M shape of the modified M segment between body negative apices 188. As defined herein, a modified M segment includes a positive apex, at least one intermediate negative apex, and at least one intermediate positive apex between negative apices. The modified M segment can include additional intermediate negative apices and intermediate positive apices.

The body spring stents 180 are operably connected to the tubular graft 110 along the length of the tubular graft 110 to hold open the lumen of the tubular graft 110 when the endoluminal prosthesis 100 is deployed. The body spring stents 180 each have body positive apices 182, body intermediate negative apices 184, body intermediate positive apices 186, and body negative apices 188, all being connected in a ring pattern. Body struts 190 connect the body negative apices 188 to the body positive apices 182, first intermediate body struts 191 connect the body positive apices 182 to the body intermediate negative apices 184, second intermediate body struts 193 connect the body intermediate negative apices 184 to the body intermediate positive apices 186, and third intermediate body struts 195 connect the body intermediate positive apices 186 to the body negative apices 188.

The sealing spring stent 160 can be axially aligned with the body spring stents 180 to seal the tubular graft 110 against the luminal wall of the vessel in which the endoluminal prosthesis 100 is deployed. In one embodiment, the intermediate sealing negative apices 166 of the sealing spring stent 160 are axially aligned with the body positive apices 182 of the body spring stents 180. In another embodiment, the sealing negative apices 164 of the sealing spring stent 160 are axially aligned with the body intermediate positive apices 186 of the body spring stents 180.

The body spring stents 180 can be aligned with each other to maximize the flexibility of the endoluminal prosthesis 100. The body positive apices 182, body intermediate negative apices 184, body intermediate positive apices 186, and body negative apices 188 of one body spring stent are aligned with the same elements of the adjacent body spring stent. The varied axial position of the apices for each of the body spring stents 180 makes the endoluminal prosthesis 100 flexible and reduces infolding of the tubular graft 110 into the lumen of the endoluminal prosthesis 100.

FIG. 4 is a detailed view of an endoluminal prosthesis with iliac legs (portions) made in accordance with the present invention. The body spring stents 180 can be aligned with the bifurcation 122 between the iliac legs 120, 130 to reduce stress on the body spring stent adjacent to the bifurcation 122. The body spring stents 180 are operably connected to the tubular graft 110 along the length of the tubular graft 110 to hold open the lumen of the tubular graft 110 when the endoluminal prosthesis 100 is deployed.

The tubular graft 110 has a first iliac leg 120 and a second iliac leg 130 at the distal end 104 with an iliac bifurcation 122 between the first iliac leg 120 and the second iliac leg 130. In one embodiment, one of the body positive apices 182 of the body spring stents 180 is axially aligned with the iliac bifurcation 122. In another embodiment, one of the body intermediate positive apices 186 of the body spring stents 180 is axially aligned with the iliac bifurcation 122.

The iliac spring stents on one of the iliac legs can be aligned with the iliac spring stents of the other iliac leg to reduce the diameter of the endoluminal prosthesis 100 when the endoluminal prosthesis 100 is compressed. The iliac spring stents 190 are operably connected to the iliac legs 120, 130. The iliac spring stents 190 have iliac positive apices 192 and iliac negative apices 194 connected in a sinusoidal ring pattern by iliac struts 196. The iliac spring stents 190 for the iliac leg 120 can be aligned with the iliac spring stents 190 for the other iliac leg 130 so that the apices do not line up between one iliac leg and the other. For example, the iliac positive apices 192 of the iliac spring stents 190 on the iliac leg 120 can be circumferentially offset from the iliac positive apices 192 of the iliac spring stents 190 on the other iliac leg 130. When the iliac spring stents 190 are of the same axial height and there is an axial separation (the distance between the dashed lines representing the imaginary limits of the stent rings and the line of maximum bulk as crowns fold along the line) between adjacent iliac spring stents 190 on one leg, none of the apices align axially when the iliac spring stents 190 are circumferentially offset between the iliac legs. Compression is limited by the number of positive or negative apices aligned along a given circumference, so circumferentially offsetting the apices of the iliac spring stents 190 reduces the compressed diameter.

When the iliac legs 120, 130 are of unequal diameter when deployed, such as when an ipsilateral limb has a larger deployed diameter than a contralateral limb, the iliac spring stents 190 can be selected to cleanly open the lumen of the contralateral limb so that a guide wire can be advanced through the contralateral limb. The iliac spring stents 190 can have approximately equal unrestrained spring diameters, i.e., the diameter across the spring stent when the spring stent is uncompressed, and can be sized to provide the desired radial force to expand the larger diameter iliac leg, such as the ipsilateral limb. Because the smaller diameter iliac leg, such as the contralateral limb, has a smaller diameter, the equal diameter iliac spring stent 190 used in the smaller diameter iliac leg provides a larger radial force in the smaller diameter iliac leg. The larger radial force cleanly opens the lumen of the smaller diameter iliac leg.

Figure 5:
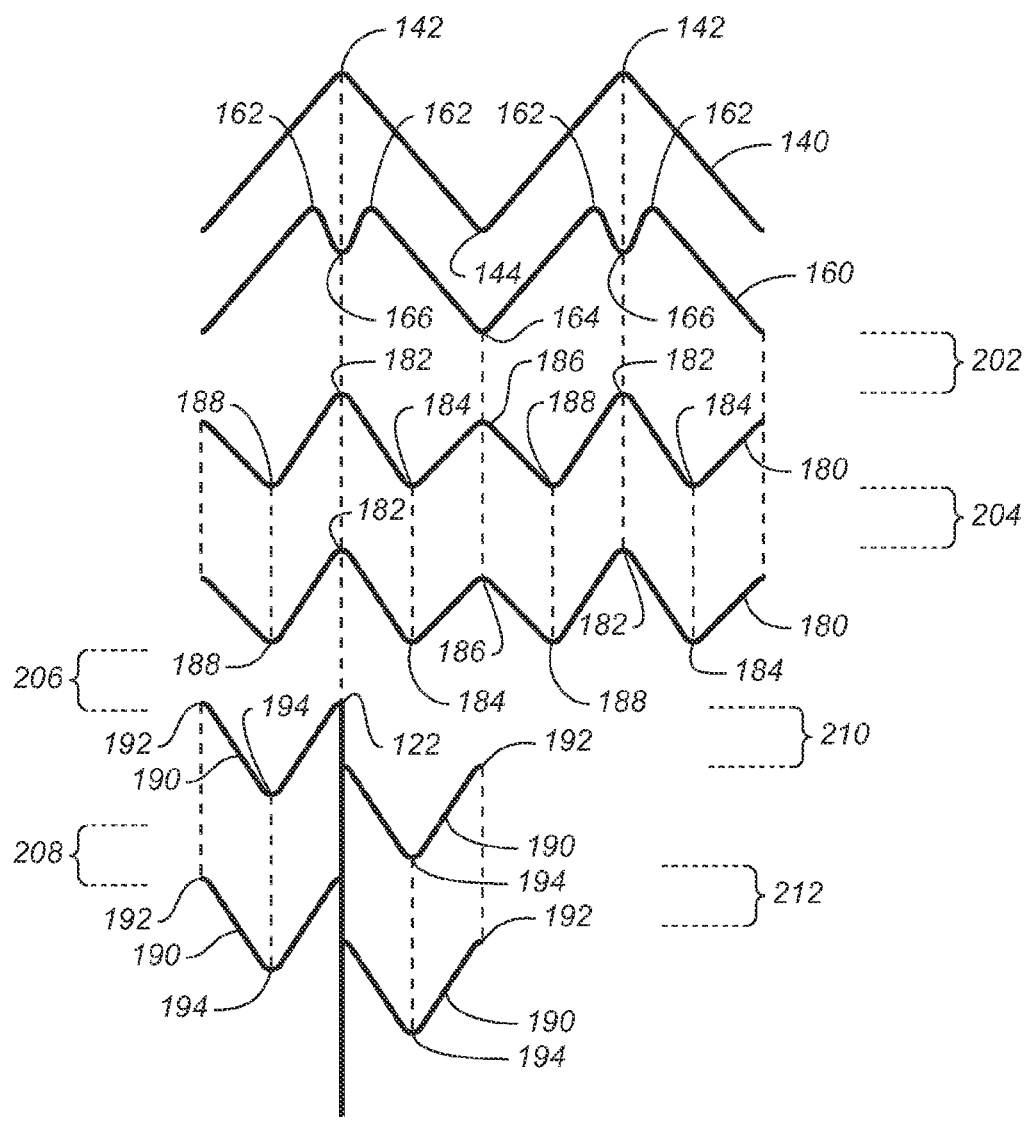
FIG. 5 is a schematic diagram of spring stent alignment for an endoluminal prosthesis with spring stents made in accordance with the present invention.

FIG. 5, in which like elements share like reference numbers with FIGS. 1-4, is a schematic diagram of spring stent alignment for an endoluminal prosthesis with spring stents made in accordance with the present invention. The spring stent alignment is selected to seal the endoluminal prosthesis against the luminal wall of the vessel in which the endoluminal prosthesis is deployed, to reduce the compressed diameter of the endoluminal prosthesis for delivery, and/or to increase the flexibility of the endoluminal prosthesis for delivery.

The suprarenal spring stent 140 and the sealing spring stent 160 are arranged to seal the tubular graft 110 with a short landing area, i.e., a short axial length sealing the tubular graft 110 against the luminal wall of the vessel. The sealing positive apices 162 of the sealing spring stent 160 is located near the proximal end 102 of the endoluminal prosthesis 100 and the axial length between the sealing positive apices 162 and the intermediate sealing negative apices 166 is small to reduce the effective sealing length. The axial length between the sealing positive apices 162 and the sealing negative apices 164 allows nesting of the suprarenal negative apices 162 with the sealing negative apices 164. In one embodiment, the suprarenal positive apices 142 are axially aligned with the intermediate sealing negative apices 166. In another embodiment, the suprarenal negative apices 162 are circumferentially offset from the sealing positive apices 162, so that the suprarenal negative apices 162 overlap the intermediate sealing struts 170, reducing the compressed diameter. In another embodiment, the suprarenal negative apices 144 are axially aligned with the sealing negative apices 164. In another embodiment, the sealing positive apices 162 are circumferentially aligned with the proximal end 102 of the tubular graft 110.

The sealing spring stent 160 and the body spring stents 180 are arranged to help seal the tubular graft 110 against the luminal wall of the vessel. In one embodiment, the intermediate sealing negative apices 166 of the sealing spring stent 160 are axially aligned with the body positive apices 182 of the body spring stents 180 to aid the intermediate sealing negative apices 166 with sealing. In another embodiment, the sealing negative apices 164 of the sealing spring stent 160 are axially aligned with the body intermediate positive apices 186 of the body spring stents 180 to aid the sealing negative apices 164 with sealing. In one embodiment, the sealing negative apices 164 are circumferentially offset from the body positive apices 182 to form a gap 202 between the sealing spring stent 160 and the proximal body spring stent 180, such as a 1 mm gap. The axial distances between the intermediate sealing negative apices 166 and the body positive apices 182 and between the sealing negative apices 164 and the body intermediate positive apices 186 provide flexibility for the endoluminal prosthesis and avoids overlap of the sealing spring stent 160 and the body spring stents 180.

The body spring stents 180 can be axially aligned with each other to increase the flexibility of the endoluminal prosthesis 100. In one embodiment, the body positive apices 182, body intermediate negative apices 184, body intermediate positive apices 186, and body negative apices 188 of one body spring stent are axially aligned with the same elements of the adjacent body spring stent. In one embodiment, the body negative apices 188 are circumferentially offset from the body positive apices 182 of the adjacent body spring stent to form a gap 204 between one body spring stent and the adjacent body spring stent, such as a 2 mm gap. The circumferential offset keeps the body spring stents 180 from overlapping. The mixed axial heights of the intermediate apices increases flexibility and reduces infolding of the tubular graft 110 into the lumen of the endoluminal prosthesis.

The body spring stents 180 can be aligned with the bifurcation 122 between the iliac legs 120, 130 to reduce stress on the body spring stent adjacent to the bifurcation 122. In one embodiment, one of the body positive apices 182 of the body spring stents 180 is axially aligned with the iliac bifurcation 122. In another embodiment, one of the body intermediate positive apices 186 of the body spring stents 180 is axially aligned with the iliac bifurcation 122. In one embodiment, the body negative apices 188 are circumferentially offset from the iliac bifurcation 122 to form a gap 206 between the distal body spring stent and the iliac bifurcation 122, such as a 2 mm gap.

The iliac spring stents can be aligned with the iliac bifurcation 122 and with other iliac spring stents on the same iliac leg to avoid overlap when the endoluminal prosthesis is in a compressed state. In one embodiment, the proximal iliac positive apices 192 are circumferentially aligned with the iliac bifurcation 122. In another embodiment, the iliac negative apices 194 are circumferentially offset from the iliac positive apices 192 of the adjacent iliac spring stent to form a gap 208 between the adjacent iliac spring stents, such as a 2.5 mm gap. In another embodiment, the proximal iliac positive apices 192 are circumferentially offset from the iliac bifurcation 122 to form a gap 210 between the iliac positive apices 192 and the iliac bifurcation 122, such as a 2 mm gap. In another embodiment, the iliac negative apices 194 are circumferentially offset from the iliac positive apices 192 of the adjacent iliac spring stent to form a gap 212 between the adjacent iliac spring stents, such as a 3 mm gap.

The iliac spring stents on one of the iliac legs can be aligned with the iliac spring stents of the other iliac leg to reduce the diameter of the endoluminal prosthesis 100 when the endoluminal prosthesis 100 is compressed. In one embodiment, the iliac positive apices 192 of the iliac spring stents 190 on the iliac leg 120 can be circumferentially offset from the iliac positive apices 192 of the iliac spring stents 190 on the other iliac leg 130, so that the iliac positive apices 192 of one iliac leg overlap the iliac struts 196 of the other iliac leg.

Those skilled in the art will appreciate that any combination of the alignments of FIG. 5 can be used as desired for a particular application.

Figure 6:
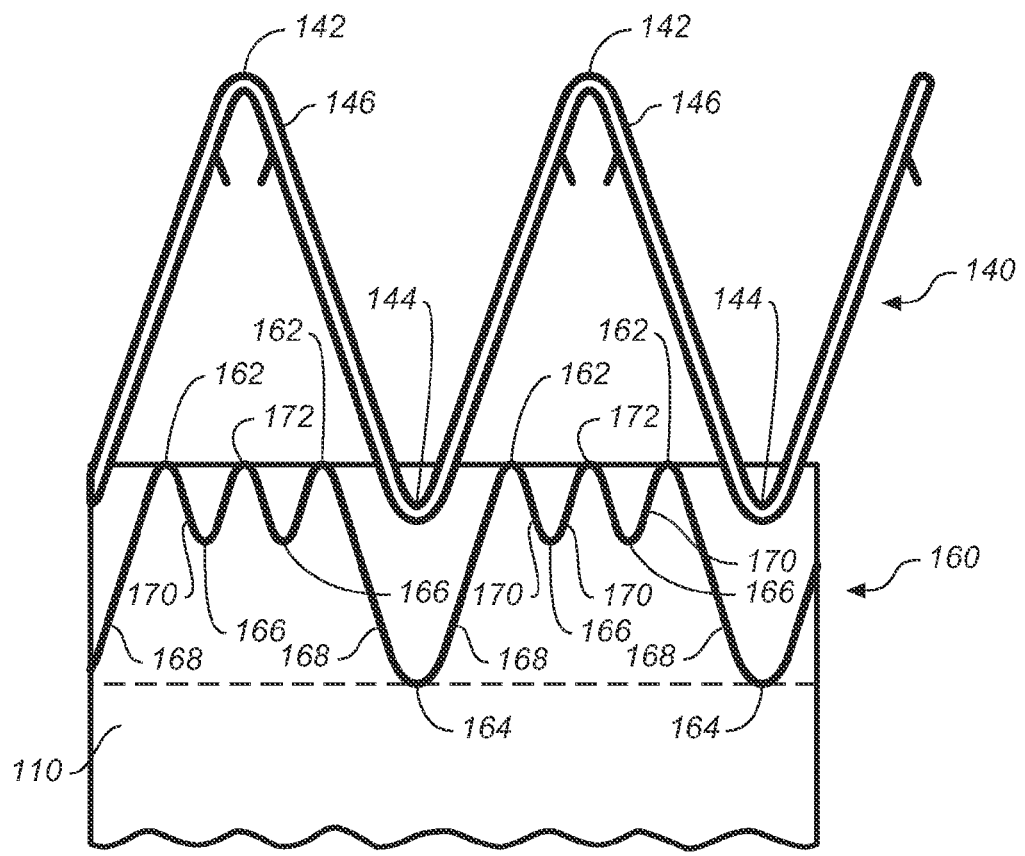
FIG. 6 is a detailed view of an endoluminal prosthesis with another embodiment of a sealing spring stent made in accordance with the present invention.

FIG. 6, in which like elements share like reference numbers with FIGS. 1-5, is a detailed view of an endoluminal prosthesis with another embodiment of a sealing spring stent made in accordance with the present invention. In this embodiment, the M shape of the spring stent of FIG. 2 includes additional intermediate sealing negative apices 166 and intermediate sealing positive apices 172. Additional intermediate sealing struts 170 connect the intermediate sealing negative apices

166 and intermediate sealing positive apices 172. Those skilled in the art will appreciate that more than one intermediate sealing negative apex 166 and more than two intermediate sealing positive apices 172 can be placed between adjacent sealing struts 168 as desired for a particular application.

Figure 7:
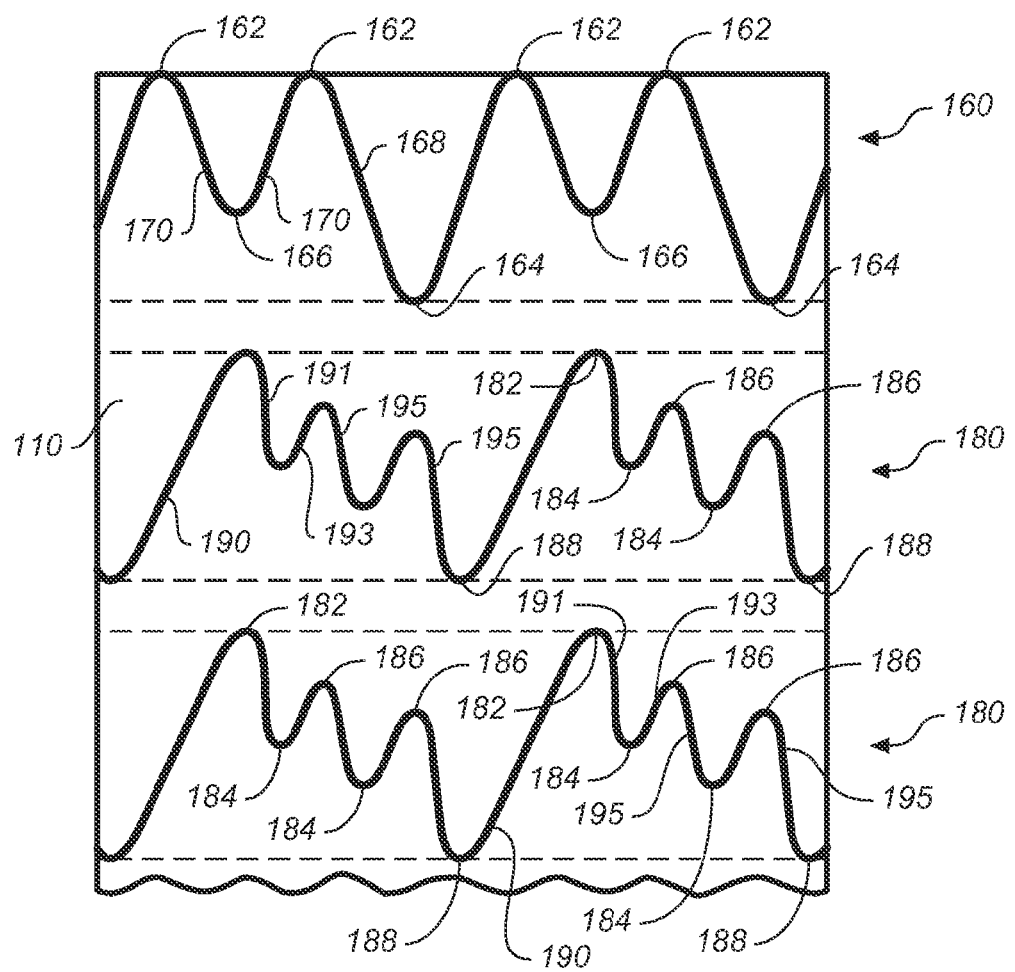
FIG. 7 is a detailed view of an endoluminal prosthesis with another embodiment of body spring stents made in accordance with the present invention.

FIG. 7, in which like elements share like reference numbers with FIGS. 1-5, is a detailed view of an endoluminal prosthesis with another embodiment of body spring stents made in accordance with the present invention. In this embodiment, the modified M shape of the spring stent of FIG. 3 includes additional body intermediate positive apices 186 and body intermediate negative apices 184 connected by additional intermediate body struts 195. Those skilled in the art will appreciate that more than two body intermediate positive apices 186 and more than two body intermediate negative apices 184 can be placed between adjacent body positive apices 182 and body negative apices 188 as desired for a particular application.

The endoluminal prosthesis is delivered to the aneurysm in a compressed condition and allowed to expand or expanded. For the example of an abdominal aortic aneurysm, a catheter is advanced to the abdominal aortic aneurysm through the femoral artery, the carotid artery, or the subclavian artery. The catheter is guided to the location of the aneurysm with X-ray or fluoroscopic data and the endoluminal prosthesis advanced to the aneurysm through the catheter. When endoluminal prosthesis is outside the catheter and in the aneurysm, the endoluminal prosthesis can be allowed to expand or expanded. In one embodiment, the spring stents of the endoluminal prosthesis are made of a shape memory alloy, such as nitinol, that expands the endoluminal prosthesis to a predetermined shape when the spring stents are released from a surrounding sheath and exposed to body temperature. In another embodiment, the spring stents of the endoluminal prosthesis are made of elastic alloy and held compressed with dissolvable ties. The dissolvable ties dissolve and the endoluminal prosthesis expands when the dissolvable ties are exposed to the fluid in the vessel. In another embodiment, the spring stents of the endoluminal prosthesis are made of deformable alloy and expanded with a balloon, such as a balloon used in percutaneous transluminal coronary angioplasty (PTCA). Those skilled in the art will appreciate that the endoluminal prosthesis can be used with any vessel in the body and is not limited to use with aneurysms.

While specific embodiments of the invention are disclosed herein, various changes and modifications can be made without departing from the spirit and scope of the invention. The scope of the invention is indicated in the appended claims, and all changes that come within the meaning and range of equivalents are intended to be embraced therein.

The invention claimed is:

1. An endoluminal prosthesis comprising:
   a tubular graft having a proximal end and a distal end;
   a suprarenal spring stent operably connected to the proximal end, the suprarenal spring stent having suprarenal positive apices and suprarenal negative apices connected in a sinusoidal ring pattern by suprarenal struts;
   a sealing spring stent operably connected to the tubular graft, the sealing spring stent having sealing positive apices, sealing negative apices, and intermediate sealing negative apices connected in a ring pattern, the sealing negative apices alternating with the intermediate sealing negative apices between adjacent sealing positive apices, the sealing positive apices being connected to the sealing negative apices by sealing struts, and the sealing positive apices being connected to the intermediate sealing negative apices by intermediate sealing struts; and
   body spring stents operably connected to the tubular graft, each of the body spring stents having body positive apices, body intermediate negative apices, body intermediate positive apices, and body negative apices, connected in a ring pattern;
   wherein the suprarenal positive apices are axially aligned with the intermediate sealing negative apices; and
   body struts connect the body negative apices to the body positive apices, first intermediate body struts connect the body positive apices to the body intermediate negative apices, second intermediate body struts connect the body intermediate negative apices to the body intermediate positive apices, and third intermediate body struts connect the body intermediate positive apices to the body negative apices.

2. The endoluminal prosthesis of claim 1 wherein the suprarenal negative apices are circumferentially offset from the sealing positive apices.

3. The endoluminal prosthesis of claim 1 wherein the suprarenal negative apices are axially aligned with the sealing negative apices.

4. The endoluminal prosthesis of claim 1 wherein the intermediate sealing negative apices are axially aligned with the body positive apices.

5. The endoluminal prosthesis of claim 1 wherein the sealing negative apices are axially aligned with the body intermediate positive apices.

6. The endoluminal prosthesis of claim 1 wherein the body positive apices of one of the body spring stents are axially aligned with the body positive apices of an adjacent one of the body spring stents.

7. The endoluminal prosthesis of claim 1 wherein:
   the tubular graft has a first iliac leg and a second iliac leg at the distal end, and an iliac bifurcation between the first iliac leg and the second iliac leg; and
   one of the body positive apices is axially aligned with the iliac bifurcation.

8. The endoluminal prosthesis of claim 7 further comprising:
   first iliac spring stents operably connected to the first iliac leg, the first iliac spring stents having first iliac positive apices and first iliac negative apices connected in a sinusoidal ring pattern by first iliac struts; and
   second iliac spring stents operably connected to the second iliac leg, the second iliac spring stents having second iliac positive apices and second iliac negative apices connected in a sinusoidal ring pattern by second iliac struts;
   wherein the first iliac positive apices are circumferentially offset from the second iliac positive apices.

9. The endoluminal prosthesis of claim 7 further comprising:
   first iliac spring stents operably connected to the first iliac leg, the first iliac spring stents having first iliac positive apices and first iliac negative apices connected in a sinusoidal ring pattern by first iliac struts; and
   second iliac spring stents operably connected to the second iliac leg, the second iliac spring stents having second iliac positive apices and second iliac negative apices connected in a sinusoidal ring pattern by second iliac struts;
   wherein deployed diameters of the first iliac leg and the second iliac leg are unequal, and unrestrained spring diameters of the first iliac spring stents and the second iliac spring stents are approximately equal.

10. The endoluminal prosthesis of claim 9 wherein the unrestrained spring diameter is selected to provide a desired radial force on the larger of the first iliac leg and the second iliac leg.

11. The endoluminal prosthesis of claim 1 wherein:
the tubular graft has a first iliac leg and a second iliac leg at the distal end, and an iliac bifurcation between the first iliac leg and the second iliac leg; and
one of the body intermediate positive apices is axially aligned with the iliac bifurcation.

12. An endoluminal prosthesis comprising:
a tubular graft having a proximal end and a distal end, the tubular graft having a first iliac leg and a second iliac leg at the distal end, and an iliac bifurcation between the first iliac leg and the second iliac leg;
a suprarenal spring stent operably connected to the proximal end, the suprarenal spring stent having suprarenal positive apices and suprarenal negative apices connected in a sinusoidal ring pattern by suprarenal struts;
body spring stents operably connected to the tubular graft, each of the body spring stents having body positive apices, body intermediate negative apices, body intermediate positive apices, and body negative apices, connected in a ring pattern;
first iliac spring stents operably connected to the first iliac leg, the first iliac spring stents having first iliac positive apices and first iliac negative apices connected in a sinusoidal ring pattern by first iliac struts; and
second iliac spring stents operably connected to the second iliac leg, the second iliac spring stents having second iliac positive apices and second iliac negative apices connected in a sinusoidal ring pattern by second iliac struts;
wherein body struts connect the body negative apices to the body positive apices, first intermediate body struts connect the body positive apices to the body intermediate negative apices, second intermediate body struts connect the body intermediate negative apices to the body intermediate positive apices, and third intermediate body struts connect the body intermediate positive apices to the body negative apices;
one of the body positive apices is axially aligned with the iliac bifurcation; and
deployed diameters of the first iliac leg and the second iliac leg are unequal, and unrestrained spring diameters of the first iliac spring stents and the second iliac spring stents are approximately equal.

13. The endoluminal prosthesis of claim 12 wherein the body positive apices of one of the body spring stents are axially aligned with the body positive apices of an adjacent one of the body spring stents.

14. The endoluminal prosthesis of claim 12 further comprising:
first iliac spring stents operably connected to the first iliac leg, the first iliac spring stents having first iliac positive apices and first iliac negative apices connected in a sinusoidal ring pattern by first iliac struts; and
second iliac spring stents operably connected to the second iliac leg, the second iliac spring stents having second iliac positive apices and second iliac negative apices connected in a sinusoidal ring pattern by second iliac struts;
wherein the first iliac positive apices are circumferentially offset from the second iliac positive apices.

15. The endoluminal prosthesis of claim 12 wherein the unrestrained spring diameter is selected to provide a desired radial force on the larger of the first iliac leg and the second iliac leg.

16. The endoluminal prosthesis of claim 12 wherein
one of the body intermediate positive apices is axially aligned with the iliac bifurcation.

17. The endoluminal prosthesis of claim 12 further comprising:
a sealing spring stent operably connected to the tubular graft, the sealing spring stent having sealing positive apices, sealing negative apices, and intermediate sealing negative apices connected in a ring pattern, the sealing negative apices alternating with the intermediate sealing negative apices between adjacent sealing positive apices, the sealing positive apices being connected to the sealing negative apices by sealing struts, and the sealing positive apices being connected to the intermediate sealing negative apices by intermediate sealing struts;
wherein the suprarenal positive apices are axially aligned with the intermediate sealing negative apices.

18. The endoluminal prosthesis of claim 17 wherein the suprarenal negative apices are circumferentially offset from the sealing positive apices.

19. The endoluminal prosthesis of claim 17 wherein the suprarenal negative apices are axially aligned with the sealing negative apices.

20. The endoluminal prosthesis of claim 17 wherein the intermediate sealing negative apices are axially aligned with the body positive apices.

21. The endoluminal prosthesis of claim 17 wherein the sealing negative apices are axially aligned with the body intermediate positive apices.

22. An endoluminal prosthesis comprising:
a tubular graft having a proximal end and a distal end, the tubular graft having a first iliac leg and a second iliac leg at the distal end, and an iliac bifurcation between the first iliac leg and the second iliac leg;
a suprarenal spring stent operably connected to the proximal end, the suprarenal spring stent having suprarenal positive apices and suprarenal negative apices connected in a sinusoidal ring pattern by suprarenal struts; and
body spring stents operably connected to the tubular graft, each of the body spring stents having body positive apices and body negative apices connected in a ring pattern with body struts, the body spring stents further comprising body intermediate negative apices, and body intermediate positive apices;
wherein one of the body positive apices is axially aligned with the iliac bifurcation; and
the body struts connect the body negative apices to the body positive apices, first intermediate body struts connect the body positive apices to the body intermediate negative apices, second intermediate body struts connect the body intermediate negative apices to the body intermediate positive apices, and third intermediate body struts connect the body intermediate positive apices to the body negative apices, in a ring pattern.

23. The endoluminal prosthesis of claim 22 further comprising:
first iliac spring stents operably connected to the first iliac leg, the first iliac spring stents having first iliac positive apices and first iliac negative apices connected in a sinusoidal ring pattern by first iliac struts; and
second iliac spring stents operably connected to the second iliac leg, the second iliac spring stents having second iliac positive apices and second iliac negative apices connected in a sinusoidal ring pattern by second iliac struts;

wherein the first iliac positive apices are circumferentially offset from the second iliac positive apices.

24. The endoluminal prosthesis of claim 22 further comprising:

first iliac spring stents operably connected to the first iliac leg, the first iliac spring stents having first iliac positive apices and first iliac negative apices connected in a sinusoidal ring pattern by first iliac struts; and second iliac spring stents operably connected to the second iliac leg, the second iliac spring stents having second iliac positive apices and second iliac negative apices connected in a sinusoidal ring pattern by second iliac struts;

wherein deployed diameters of the first iliac leg and the second iliac leg are unequal, and unrestrained spring diameters of the first iliac spring stents and the second iliac spring stents are approximately equal.

25. The endoluminal prosthesis of claim 24 wherein the unrestrained spring diameter is selected to provide a desired radial force on the larger of the first iliac leg and the second iliac leg.

26. The endoluminal prosthesis of claim 22 wherein the body positive apices of one of the body spring stents are axially aligned with the body positive apices of an adjacent one of the body spring stents.

27. The endoluminal prosthesis of claim 22 further comprising:

a sealing spring stent operably connected to the tubular graft, the sealing spring stent having sealing positive apices, sealing negative apices, and intermediate sealing negative apices connected in a ring pattern, the sealing negative apices alternating with the intermediate sealing negative apices between adjacent sealing positive apices, the sealing positive apices being connected to the sealing negative apices by sealing struts, and the sealing positive apices being connected to the intermediate sealing negative apices by intermediate sealing struts;

wherein the suprarenal positive apices are axially aligned with the intermediate sealing negative apices.

28. The endoluminal prosthesis of claim 27 wherein the suprarenal negative apices are circumferentially offset from the sealing positive apices.

29. The endoluminal prosthesis of claim 27 wherein the suprarenal negative apices are axially aligned with the sealing negative apices.

30. The endoluminal prosthesis of claim 27 wherein the intermediate sealing negative apices are axially aligned with the body positive apices.

31. The endoluminal prosthesis of claim 27 wherein the sealing negative apices are axially aligned with the body intermediate positive apices.

32. An endoluminal prosthesis comprising:

a tubular graft having a proximal end;

a suprarenal spring stent operably connected to the proximal end; and a sealing M spring stent operably connected to the tubular graft, the sealing M spring stent having M segments connected in a ring;

wherein the sealing M spring stent nests with the suprarenal spring stent.

33. The endoluminal prosthesis of claim 32 wherein each of the M segments comprises:

a first sealing negative apex connected to a first sealing positive apex by a first sealing strut;

an intermediate sealing negative apex connected to the first sealing positive apex by a first intermediate sealing strut;

a second sealing positive apex connected to the intermediate sealing negative apex by a second intermediate sealing strut; and a second sealing negative apex connected to the second sealing positive apex by a second sealing strut.

34. The endoluminal prosthesis of claim 32 wherein each of the M segments comprises:

a first sealing negative apex connected to a first sealing positive apex by a first sealing strut;

a first intermediate sealing negative apex connected to the first sealing positive apex by a first intermediate sealing strut;

an intermediate sealing positive apex connected to the first intermediate sealing negative apex by a second intermediate sealing strut;

a second intermediate sealing negative apex connected to the intermediate sealing positive apex by a third intermediate sealing strut;

a second sealing positive apex connected to the second intermediate sealing negative apex by a fourth intermediate sealing strut; and a second sealing negative apex connected to the second sealing positive apex by a second sealing strut.

35. An endoluminal prosthesis comprising:

a tubular graft having a proximal end;

a suprarenal spring stent operably connected to the proximal end; and modified M body spring stents operably connected to the tubular graft, each of the modified M body spring stents having modified M segments connected in a ring.

36. The endoluminal prosthesis of claim 35 wherein each of the modified M segments comprises:

a first body negative apex connected to a body positive apex by a body strut;

an intermediate body negative apex connected to the body positive apex by a first intermediate body strut;

an intermediate body positive apex connected to the intermediate body negative apex by a second intermediate body strut; and a second body negative apex connected to the intermediate body positive apex by a third intermediate body strut.

37. The endoluminal prosthesis of claim 35 wherein each of the modified M segments comprises:

a first body negative apex connected to a body positive apex by a body strut;

a first intermediate body negative apex connected to the body positive apex by a first intermediate body strut;

a first intermediate body positive apex connected to the first intermediate body negative apex by a second intermediate body strut;

a second intermediate body negative apex connected to the first intermediate body positive apex by a third intermediate body strut;

a second intermediate body positive apex connected to the second intermediate body negative apex by a fourth intermediate body strut; and a second body negative apex connected to the second intermediate body positive apex by a fifth intermediate body strut.

* * * * *